United States Patent [19]

Hara et al.

[11] Patent Number: 5,670,154
[45] Date of Patent: Sep. 23, 1997

[54] REDUCING TYROSINASE ACTIVITY

[75] Inventors: Yukihiko Hara; Miwa Honda, both of Fujieda, Japan

[73] Assignee: Mitsui Norin Co., Ltd., Tokyo, Japan

[21] Appl. No.: 349,477

[22] Filed: Dec. 2, 1994

Related U.S. Application Data

[63] Continuation of Ser. No. 179,582, Jan. 10, 1994, abandoned.
[51] Int. Cl.⁶ ........................................ A61K 35/78
[52] U.S. Cl. ........................ 424/195.1; 514/456; 514/783; 549/399
[58] Field of Search ................. 424/195.1; 435/184; 514/783, 456; 549/399

[56] References Cited

U.S. PATENT DOCUMENTS

| | | | |
|---|---|---|---|
| 4,585,738 | 4/1986 | Roland | 435/176 |
| 4,613,672 | 9/1986 | Hara | 549/399 |
| 4,673,530 | 6/1987 | Hara | 252/398 |
| 4,840,966 | 6/1989 | Hara et al. | 514/456 |
| 4,913,909 | 4/1990 | Hara et al. | 424/688 |
| 4,946,950 | 8/1990 | Hara et al. | 536/4.1 |
| 5,104,901 | 4/1992 | Shimamura | 514/783 |
| 5,135,957 | 8/1992 | Shimamura | 514/738 |
| 5,137,922 | 8/1992 | Shimamara et al. | 514/371 |
| 5,204,089 | 4/1993 | Hara et al. | 424/58 |
| 5,318,986 | 6/1994 | Hara et al. | 514/456 |

FOREIGN PATENT DOCUMENTS

| | | |
|---|---|---|
| 61-130285 | 6/1986 | Japan . |
| 06065085 | 3/1994 | Japan . |

OTHER PUBLICATIONS

The Merck Index 9th ed. 1976, p. 243, No. 1898.

*Primary Examiner*—Gary L. Kunz
*Assistant Examiner*—Howard C. Lee
*Attorney, Agent, or Firm*—Frishauf, Holtz, Goodman, Langer & Chick, P.C.

[57] ABSTRACT

A tyrosinase inhibiting agent acts specifically on tyrosinase to inhibit it; the effective component of this action being an inhibitor of tyrosinase consisting of tea polyphenols.

6 Claims, No Drawings

REDUCING TYROSINASE ACTIVITY

This application is a continuation of application Ser. No. 08/179,582, filed Jan. 10, 1994, now abandoned.

BACKGROUND OF THE INVENTION

1. Field of the Invention

This invention relates to tyrosinase activity inhibitor.

2. Description of the Prior Art

Tyrosinase is an enzyme which oxidatively polymerizes tyrosine and this is thought to play a part in the development of dark colored melanin. Therefore, it can be assumed that the inhibition of tyrosinase could prevent the formation of melanin. Further, it is expected that if a tyrosinase inhibiting agent is mixed into creams, lotions or other such cosmetics and applied topically to the skin, or if it is ingested internally in the form of a tablet, capsule, powder or the like, then it will be effective in preventing the development of melanin on the skin.

SUMMARY OF THE INVENTION

The present invention relates to tyrosinase activity inhibitor. In particular, the present invention relates to tyrosinase activity inhibitor containing tea polyphenols as an effective component.

DETAILED DESCRIPTION OF THE PREFERRED EMBODIMENTS

Thus the present inventors have developed an enzyme inhibitor which is free of any side effects and which will inhibit the activity of tyrosinase.

Rather than using chemically synthesized substances, the present inventors conducted various research in order to find effective natural inhibitors, and as a result discovered that the said substances were contained in tea polyphenols. That is to say, the present invention relates to a tyrosinase inhibiting agent containing tea polyphenols as the effective ingredient.

Tea polyphenols, the main components of the tyrosinase inhibiting agent of the present invention, include tea catechins of the following general formula 1.

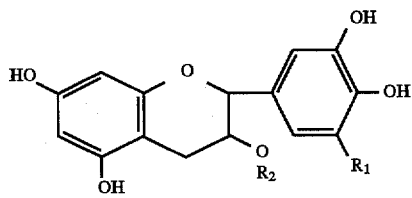

(Where $R_1$ represents H or OH and $R_2$ represents H or

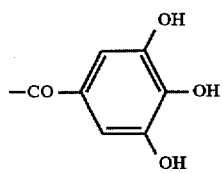

Examples of catechins of the above formula 1 are as follows:

(−)Epicatechin (in formula 1, $R_1$=H, $R_2$=H)
(−)Epigallocatechin (in formula 1, $R_1$=OH, $R_2$=H)
(−)Epicatechin gallate (in formula 1, $R_1$=H, $R_2$=

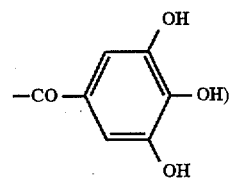

(−)Epigallocatechin gallate (in formula 1, $R_1$=OH, $R_2$=

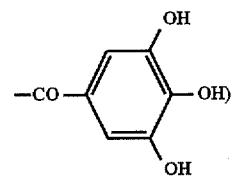

The above described tea polyphenols can be prepared from the raw material, tea leaves, and a method for the preparation thereof is described in U.S. Pat. Nos. 4,613,672, and 4,673,530, and Japanese Patent Kokai 61-130285.

The effective tyrosinase inhibiting component of the present invention, tea polyphenols, may be used singularly or it may be combined with a suitable excipient such as gelatin, sodium alginic etc.; and combined with a solvent such as water or alcohol and a diluent such as carboxymethyl cellulose before use. When the tyrosinase inhibiting agent of the present invention is used in cosmetics it should be added so that the final concentration falls between 0.01–10%.

The tyrosinase inhibitor of the present invention consists of a natural substance extracted from tea, a beverage which is commonly consumed in considerable amounts daily, and therefore there is no fear of harmful side effects to the body. Moreover, the tyrosinase inhibitor of the present invention is markedly effective even when used in low concentrations. Thus the tyrosinase inhibitor of the present invention may be added to cosmetic products etc. to inhibit tyrosinase activity.

EXAMPLES

The present invention will be explained in more detail by way of the following examples.

Example 1

The level of tyrosinase, inhibition was measured according to the following method.

50 µl of the enzyme (8300 U/ml) (Source:mushroom, SIGMA) was added to a mixture of 250 µl of tyrosine substrate solution (0.3 mg/ml), 250 µl of the inhibiting (polyphenol) solution (0.5 mg/ml), 250 µl of MacIlvain buffer solution and left for 30 minutes at 37° C. After this time the absorbance of the red colored Dopa-Chroma formed was measured at 475 nm. The following equation shows the method of calculating the effectiveness of the inhibiting action.

$$\text{Inhibition}(\%)=[(A-B)-(C-D)]/(A-B)\times 100$$

Where A, B, C, D represent the absorbance of solutions A, B, C and D as defined below, measured at 475 nm respectively.

A is the tyrosine+enzyme solution
B is the tyrosine solution
C is the tyrosine+enzyme+polyphenol solution
D is the tyrosine+polyphenol solution Each individual tea polyphenol of the tyrosinase inhibiting agent is shown in Table 1. The effectiveness of each component in the inhibiting agent was determined according to the method above. The results are shown in Table 1.

TABLE 1

| Inhibitory Agent (0.15mg/ml) | Inhibition (%) |
|---|---|
| Epicatechin | 11.9 |
| Epigallocatechin | 17.5 |
| Epicatechin gallate | 95.1 |
| Epigallocatechin gallate | 79.5 |

As shown in the table, it was confirmed that among these catechins, epicatechin gallate and epigallocatechin gallate were the strongest inhibitors of tyrosinase.

What is claimed is:

1. A method of reducing tyrosinase activity in human skin comprising topically administering to a human an effective tyrosinase activity reducing amount of at least one tea polyphenol selected from the group consisting of epigallocatechin gallate, epicatechin gallate and epigallocatechin.

2. The method according to claim 1, wherein the tea polyphenol is in a formulation selected from the group consisting of a cream, a lotion and a cosmetic.

3. The method according to claim 2, wherein the formulation is a cosmetic and the tea polyphenol is contained in the cosmetic in an amount of 0.01 to 10 wt. %.

4. The method according to claim 1, wherein the tea polyphenol is epicatechin gallate.

5. The method according to claim 1, wherein the tea polyphenol is epigallocatechin gallate.

6. The method according to claim 1, wherein the tea polyphenol is epigallocatechin.

* * * * *